United States Patent [19]

Shuman

[11] Patent Number: 5,252,566
[45] Date of Patent: Oct. 12, 1993

[54] ANTITHROMBOTIC AGENTS

[75] Inventor: Robert T. Shuman, Greenwood, Ind.

[73] Assignee: Eli Lilly and Company, Indianapolis, Ind.

[21] Appl. No.: 962,421

[22] Filed: Oct. 16, 1992

Related U.S. Application Data

[63] Continuation-in-part of Ser. No. 790,885, Nov. 12, 1991.

[51] Int. Cl.$^5$ .................. A61K 31/47; A61K 31/395; C07D 227/04; C07D 205/04
[52] U.S. Cl. ..................................... 514/210; 546/208; 546/141; 546/145; 548/482; 548/953
[58] Field of Search .................. 548/953; 514/210; 546/208

[56] References Cited

U.S. PATENT DOCUMENTS

| | | | |
|---|---|---|---|
| 4,316,889 | 2/1982 | Bajusz et al. | 260/112.5 |
| 4,346,078 | 8/1982 | Bajusz et al. | 424/177 |
| 4,399,065 | 8/1983 | Bajusz et al. | 260/112.5 |
| 4,478,745 | 10/1984 | Bajusz et al. | 530/331 |
| 4,703,036 | 10/1987 | Bajusz et al. | 530/331 |
| 5,053,392 | 10/1991 | Klein | 530/331 |

OTHER PUBLICATIONS

Bagusz, S., et al., J. Med. Chem., 1990, 33, 1729–1735.
Fareed, J., et al., Annals N.Y. Acad. of Sci. 1981, 765–784.
Schuman, et al., Proceedings of the Twelfth American Peptide Symposium, Jun. 16–21, 1991.
Wilson, et al., American Heart Association, Nov. 11–14, 1991, Anaheim Convention Center, Anaheim, Calif.
Bajusz, et al., Int. J. Peptide Res., 12, 1978, 217–221.
Gesellchen, et al., Tenth American Peptide Symposium, May 23–28, 1987, St. Louis, Mo.
Claeson, et al., Proceedings of the Twelfth American Peptide Symposium, Jun. 16–21, 1991, Cambridge, Mass.
Smith, G. F., Shuman, R. T., Gesellchen, P. D., Craft, T. J., Gifford, P., Kurz, K. D., Jackson, C. V., Sandusky, G. E., and P. D. Williams. A New Family of Thrombin Inhibitors with Improved Specificity and Therapeutic Index. (Submitted to the American Heart Association, Oct., 1991, Circulation, Oct., 1991, vol. 84, II-579 1991.).
Jackson, V., Wilson, H., Frank, J., Crowe, V., Craft, T., and G. Smith. The Thrombin Inhibitor, methyl-D--Phe-Pro-Arginal=An Effective Adjunct to Coronary Artery Thrombolysis in the Anesthetized Dog. FASEB J. 5(4)A521 (1991).
Crowe, V., Frank, J., Wilson, H., Coffman, B., Smith, G., and V. Jackson. Anticoagulant and Antithrombotic Efficacy of the Trombin Inhibitor methyl-D-Phe--Pro-Arginal in a Canine Model of Coronary Thrombosis. FASEB J. 5(4)A521 (1991).
Wilson, H., Frank, J., Crowe, V., Coffman, B., Smith, G., Shuman, R., and V. Jackson. Anticoagulant and Antithrombotic Efficacy of the Novel Thrombin Inhibitor, Methyl-D-Phg-Pro-Arginal, in a Canine Model of Coronary Thrombosis. (Arteriosclerosis and Thrombosis, Oct., 1991).

(List continued on next page.)

Primary Examiner—Mark L. Berch
Assistant Examiner—Pavanaram K. Sripada
Attorney, Agent, or Firm—David E. Boone; Leroy Whitaker

[57] ABSTRACT

Thrombin inhibitors represented by the formula

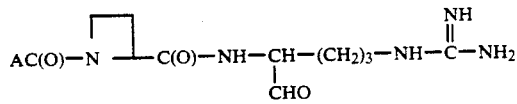

as provided wherein A is e.g. phenylglycyl, and phenylalanyl, α-methylphenylalanine and α-methylphenylglycine wherein the amino group is preferably substituted with lower alkyl alkanoyl or lower alkoxycarbonyl, or a bicyclo group e.g. 1,2,3,4-tetrahydroisoquinolin-1-yl. Also provided are a method for inhibiting clot formation in man and animals, pharmaceutical formulations useful in the method and intermediates for the inhibitors.

24 Claims, No Drawings

OTHER PUBLICATIONS

Jackson, V., Wilson, H., Frank, J., Crowe, V., Coffman, B., Craft, T., Shuman, R., and G. Smith. The Novel Thrombin Inhibitor Methyl-D-Phg-Pro-Arginal: An Effective Conjunctive Agent to Coronary Artery Thrombolysis in the Anesthetized Dog. (Arteriosclerosis and Thrombosis, Oct., 1991).

Shuman, R. T., Rothenberger, R. B., Campbell, C. S., Smith, G. F. Jackson, C. V. Kurz, K. D., and P. D. Gesellchen. Prevention of Reocclusion By a Thrombin Inhibitor. (American Peptide Symposium. in press, Jun., 1991).

Shuman, R. T., Rothenberger, R. B., Campbell, C. S., Smith, G. F., Jackson, C. V., Jurz, K. D., and P. D. Gesellchen. A Series of Highly Active Serine Proteinase Inhibitors. (American Peptide Symposium, in press, Jun., 1991).

Jackson, C. V., Frank, J. D., Crowe, V. G., Craft, T. J., and G. F. Smith. Assessment of the Anticoagulant and Antithrombotic Efficacy of the Thrombin Inhibitor, BOC-Phe-Pro-Arginal, in a Canine Model of Coronary Thrombosis. Arteriosclerosis 10 922A (1990).

Jackson, C. V., Frank, J. D., Crowe, V. G., Craft, T. J., and G. F. Smith. The Thrombin Inhibitor, BOC-Phe-Pro-Arginal. An Effective Adjunct to Coronary Artery Thrombolysis in the Anesthetized Dog. Arteriosclerosis 10 923a (1990).

Shackelford, K. A., Tanzer, R. L., Shuman, R., Gesellchen, P. D., Grindey, G. B., Sundboom, J. L., Smith, G. F., and R. L. Merriman. Inhibition of Spantaneous Metastasis by boc-D-phe-pro-arginal. American Association for Cancer Research, San Francisco, 1989. Proc. Am. Assn. Cancer Res. 30 86, 1989.

Neubauer, B. L., Clemens, J. A., Gesellchen, P. D., Hirsch, K. S., Hoover, D. M., Merriman, R. L., and G. F. Smith. Endocrine Characterization and Sensitivity of the PAIII Prostatic Adenocarcinoma in Male Lobund Wistar (LW) Rats to Anti-fibrin Agents. American Association for Cancer Research. New Orleans, May 1988. Proc. Am. Assn. Cancer Res. 29 240 (1988).

Neubauer, B. L., Best, K. L., Gesellchen, P. D., Goode, R. L., Merriman, R. L., Tanzer, L. R., Sharr, C. J., Shuman, R., Sundboom, J. L. and G. F. Smith. Inhibitory Effects of Heparin and BOC-D-PHE-PRO-ARGINAL on the metastasis of the PAIII Prostatic Adenocarcinoma in Male Lobund Wistar (LW) Rats. American Urological Association. Boston, May 1988. J. Urol. 139 175A (1988).

Gesellchen, P. D., Smith, G. F., et al. Anticoagulant, antithrombotic, and antimetastatic effects of a serine proteinase inhibitor. 10th American Peptide Symposium, Washington University, St. Louis, Mo. (1987).

Smith, G. F., Sundboom, J. L., Best, K., Gesellchen, P. D., Merriman, R. L., Shuman, R., and Neubauer, B. L. Heparin, Boc-D-Phe-Pro-Arginal, and Warfarin (Fibrin Antagonists) Inhibit Metastasis in an *In Vivo* Model. American Chemical Society National Meeting. Abstract BIOL 70 Biochemistry (1987).

K. D. Kurz, T. Smith, R. A. Moore, and B. W. Main. Comparison of Thrombin Inhibitors in Rat Models of Thrombosis and Thrombolysis. FASEB Journal, vol. 5 (No. 4), 1991.

５,252,566

1

ANTITHROMBOTIC AGENTS

This is a continuation-in-part of application Ser. No. 07/790,885, filed Nov. 12, 1991 now pending.

BACKGROUND OF THE INVENTION

This invention relates to inhibitors of thrombin which are useful in the prevention of clot formation in warm blooded mammals. In particular, it relates to N-phenylalanyl and N-phenylglyclyl derivatives of the dipeptide of L-azetidine-2-carboxylic acid and L-arginine aldehyde and to derivatives and salts thereof.

Thrombin inhibition is currently treated by the administration of heparins and coumarins e.g. warfarin. The mechanism by which these agents act has been the subject of extensive study. Heparins are administered parenterally and levels of the drug must be carefully monitored to control unwanted bleeding in the patient. Coumarins act by blocking or inhibiting the formation of prothrombin and generally require some time to achieve effectiveness. One regime of treatment e.g. of phlebitis utilizes heparin initially followed by coumarin. Although both of these agents are effective, there remains a need for thrombin inhibitors which act quickly to prevent clot formation and which do not interfere with the action of plasmin in the dissolution of existing clots or with administered clot lysing agents such as tissue plasminogen activators.

SUMMARY OF THE INVENTION

The thrombin inhibitors provided by this invention are represented by the following formula 1.

$$AC(O)-N\overset{L}{\underset{}{\boxed{\phantom{xx}}}}C(O)-NH-\underset{CHO}{\overset{L}{\underset{|}{CH}}}-(CH_2)_3-NH-\overset{NH}{\underset{}{\overset{\|}{C}}}-NH_2 \quad 1$$

wherein A is 1) a group of the formula $$R-\underset{B}{\overset{R_1}{\underset{|}{C}}}-$$

wherein R is a phenyl group of the formula

<chemical structure: phenyl ring with substituents a, a' and $-(CH_2)_n-$> wherein a and a' independently are hydrogen, lower alkyl, lower alkoxy, halogen, trifluoromethyl, hydroxy, hydroxymethyl, amino, or aminomethyl; and n is 0 or 1; or R is thienyl, furyl, naphthyl, or naphthyl mono- or disubstituted by lower alkyl, lower alkoxy, halogen, amino, mono- or di-(lower alkyl)amino, or hydroxy; or R is cyclohexadienyl, cyclohexenyl, cyclohexyl or cyclopentyl;

$R_1$ is hydrogen, methyl or ethyl;

B is lower alkyl, lower alkoxy, hydroxy, or an amino group of the formula $-N(R_2)(R_3)$

2 wherein $R_2$ and $R_3$ independently are hydrogen or lower alkyl, or $R_2$ is hydrogen, and $R_3$ is $C_1-C_6$ alkanoyl, halo substituted $C_2-C_6$ alkanoyl, or an oxycarbonyl group of the formula $R_4-OC(O)-$ wherein $R_4$ is $C_1-C_6$ alkyl, $C_2-C_6$ alkenyl, $C_3-C_7$ cycloalkyl, benzyl, nitrobenzyl, diphenylmethyl, or a phenyl group as defined above; provided, that when $R_1$ is methyl or ethyl, B is other than methyl or ethyl;

2) a bicyclic group represented by the formula 2

<chemical structure: bicyclic ring system with $R_6$, Q, N—$R_5$, Y> 2 wherein Q is a one carbon radical represented by $$\overset{}{\underset{}{\overset{\diagdown}{\underset{\diagup}{C}}}}=O,$$

$-CH_2-$, or $$-\overset{H}{\underset{|}{C}}-,$$

or a two carbon radical represented by $-CH_2-CH_2-$, $$-CH_2-C=O, \text{ or } -CH_2-\overset{H}{\underset{|}{C}}-;$$

Y is a one carbon radical represented by $-CH_2-$, or $$-\overset{H}{\underset{|}{C}}-,$$

or a two carbon radical represented by $$-CH_2-\overset{H}{\underset{|}{C}}-;$$

provided that one, but not both, of Q and Y is $$-\overset{H}{\underset{|}{C}}-$$

or

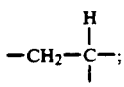

and, provided further, that only one of Q and Y is a two carbon radical;

$R_5$ is hydrogen or an oxycarbonyl group, $R_4$—OC-(O)—, as defined above, and $R_6$ is hydrogen, lower alkyl, lower alkoxy, halogen, hydroxy, trifluoromethyl, carboxy, carbamoyl, or aminosulfonyl; and the dotted lines within the 6-membered ring indicate an aromatic ring or a perhydro ring;

and the pharmaceutically acceptable, non-toxic salts thereof.

The peptides represented by the formula 1 are useful antithrombotic agents and can be used as adjuncts to tissue plasminogen activator (tPA), streptokinase or urokinase therapy.

The instant invention also comprises intermediates for the compounds of formula 1 which are represented by the following formula:

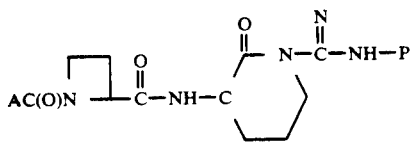

whereas A is as set forth for formula 1 above and P is an amino protecting group such as benzyl carbonate, t-butyl carbonate, p-toluenesulfonyl and the like.

The compounds are prepared by conventional coupling the dipeptide formed with L-azetidine-2-carboxylic acid and the cyclic lactam of arginine to form Boc-D-Phg-Azt-Arg lactam in amino protected form. The Arg lactam ring is, opened by reduction and the arginine amino protecting group removed to provide Boc-D-Phg-Azt-Arg aldehyde. The peptides are converted to suitable salt forms such as the acetates, hydrochlorides and sulfates.

The invention also provides a method for preventing the formation of clots in man and animals and pharmaceutical formulations useful in the method.

DETAILED DESCRIPTION

The compounds of the invention represented by the formula 1 are tripeptides when AC(O)- is an amino acid residue such as D-phenylglycyl or D-phenylalanine, and when A is other than an amino acid residue, e.g. when B is a group other than an amino or alkylamino group, the compounds are N-acyl derivatives of the dipeptide of azetidine-2-carboxylic acid and arginine aldehyde (Azt-Arg-H). The asymmetric center of the A(C=O) moiety in formula 1 is preferably R or RS while that of the azetidine and arginine aldehyde moieties is L; however, the center of A(C=O) also may be S.

The terms used in formula 1 are defined herein as follows:

Arg is arginine, Pro is proline, Phe is phenylalanine, Phg is phenylglycine, and Azt is azetidine-2-carboxylic acid.

Lower alkyl refers to the straight and branched chain $C_1$-$C_4$ alkyl groups such as methyl, ethyl, n-propyl, isopropyl, n-butyl and the like.

Lower alkoxy refers to $C_1$-$C_4$ alkoxy group such as methoxy, ethoxy, n-propoxy, isopropoxy, n-butoxy, t-butoxy and the like.

Halogen refers to fluoro, chloro, bromo or iodo.

Mono- or di-(lower alkyl)amino refers to such groups as methylamino, ethylamino, dimethylamino, methylethylamino, diethylamino, n-butylamino, n-propylamino and the like.

The term "$C_1$-$C_6$ alkanoyl" refers to the acyl moieties of the $C_1$ to $C_6$ carboxylic acids, e.g., such groups as formyl, acetyl, propionyl, butyryl, hexanoyl and the like. "Halo substituted $C_2$-$C_6$ alkanoyl" refers to the above $C_2$-$C_6$ alkanoyl groups substituted with up to three halogen atoms. Examples include, chloroacetyl, dichloroacetyl, fluoroacetyl, 4-bromobutyryl, 3,3,3-trifluoropropionyl, 3, 4-dichlorobutyryl, 3,3-dichlorohexanoyl, and like fluoro, chloro or bromo substituted $C_1$-$C_6$ alkanoyl groups. "$C_1$-$C_6$ alkyl" refers to the straight and branched alkyl groups such as the $C_1$-$C_4$ alkyl groups defined above and, in addition, n-pentyl, isopentyl, n-hexyl, the isomeric hexyl groups, and the like. "$C_2$-$C_6$ alkenyl" refers to the olefinic groups such as vinyl, allyl, butenyl, isomeric pentenyl and hexenyl groups. "$C_3$-$C_7$ Cycloalkyl" refers to the cyclic hydrocarbons having from three to 7 ring carbon atoms such as cyclopropyl, cyclobutyl, cyclopentyl, cyclohexyl and cycloheptyl.

As defined in formula 1, when A is the group $(R)(R_1)(B)C$-, R can be a phenyl or benzyl (n=1) group which may be mono- or di-substituted. Examples of such groups are phenyl (a and a'=H), benzyl (a and a=H and n=1), 4-methylphenyl, 3-ethylphenyl, 4-methoxyphenyl, 3-methoxyphenyl, 3-ethoxyphenyl, 2-methoxyphenyl, 3-isopropoxyphenyl, 4-hydroxyphenyl, 4-hydroxybenzyl, 4-chlorophenyl, 4-chlorobenzyl, 3-chlorophenyl, 2-fluorophenyl, 3-fluorophenyl, 3-bromophenyl, 4-fluorophenyl, 3-trifluoromethylphenyl, 4-trifluoromethylphenyl, 3-trifluoromethylbenzyl, 4-hydroxymethylphenyl, 2-hydroxymethylphenyl, 3-aminophenyl, 4-aminophenyl, 3-amino-4-chlorophenyl, 2,4-dimethylbenzyl, 3,4-dichlorophenyl, 3-hydroxy-4-fluorophenyl, 3-hydroxy-4-methylphenyl, 3-methoxy-4-hydroxyphenyl, 3-chloro-4-ethoxyphenyl, and like mono- or di-substituted phenyl groups.

Examples of R groups when R is naphthyl or a mono- or di-substituted naphthyl group are 1-naphthyl, 2-naphthyl, 6-methoxy-2-naphthyl, 8-hydroxy-1-naphthyl, 8-amino-2-naphthyl, 4-methyl-1-naphthyl, 6-chloro-2-naphthyl, 4-hydroxy-6-ethoxy-2-naphthyl, 8-methylamino-4-chloro-2-naphthyl, 6,8-dimethoxy-2-naphthyl, 6-ethyl-1-naphthyl, 4-hydroxy-1-naphthyl, 3-methoxy-1-naphthyl, and like naphthyl groups.

Examples of groups represented in the formula 1 when B is an amino group —$N(R_2)(R_3)$ are amino ($R_2=R_3=H$), methylamino, ethylamino, isopropylamino, dimethylamino, and like amino groups; when $R_2$ is hydrogen and $R_3$ is $C_1$-$C_6$ alkanoyl or halo-substituted $C_2$-$C_6$ alkanoyl, examples of such groups are acetyl, propionyl, hexanoyl, 2-methylpropionyl, trifluoracetyl, trichloroacetyl, 2,3-dibromopropionyl, and the like; and when $R_2$ is hydrogen and $R_3$ is an oxycarbonyl group $R_4$—O—C(O)—, examples of such groups, are the $C_1$-$C_6$ alkoxycarbonylamino groups such as methoxycarbonylamino, ethoxycarbonylamino, t-butoxycarbonylamino, isoamyloxycarbonylamino and the like; the $C_2$-$C_6$ alkenyloxycarbonylamino groups such as vinyloxycarbonylamino, allyloxycarbonylamino, 2-butenyloxycarbonylamino, and the like;

$C_3$–$C_7$ cycloalkoxycarbonylamino groups such as cyclopropyloxycarbonylamino, cyclopentyloxycarbonylamino, cyclohexyloxycarbonylamino, and the like. Oxycarbonylamino groups represented by the term B further include for example, benzyloxycarbonylamino, 4-nitrobenzyloxycarbonylamino, diphenylmethoxycarbonylamino, phenyloxycarbonylamino, or a substituted phenyloxycarbonylamino group wherein the substituted phenyl moiety is as defined hereinabove, and the like.

Examples of the groups A(C=O) of the formula 1 when A is a group 1 radical of the formula (R)($R_1$)(B)C- are phenylglycyl, phenylalanyl, 3-methoxyphenylglycyl, 4-methoxyphenylglycyl, 4-chlorophenylglycyl, 3,4-dichlorophenylglycyl, 4-chlorophenylalanyl, 3-trifluoromethylphenylglycyl, N-(t-butyloxycarbonyl)-phenylglycyl, α-methylphenylacetyl, α-ethylphenylacetyl, α-methoxyphenylacetyl, α isopropoxyphenylacetyl, 1-naphthylglycyl, 2-naphthylglycyl, N-(t-butyloxycarbonyl)-2-naphthylglycyl, 2-thienylglycyl, 3-thienylglycyl, N-(cyclopentyloxycarbonyl)-2-thienylglycyl, 2-furylglycyl, N-ethyl-2-furylglycyl, mandeloyl, 4-chloromandeloyl, 3-methoxymandeloyl, α-hydroxy-α-(2-naphthyl)acetyl, α-hydroxy-α-(2-thienyl)acetyl, 1,4-cyclohexadienylglycyl, 1-cyclohexenylglycyl, N-(t-butyloxycarbonyl)-1,4-cyclohexadienylglycyl, cyclohexyglycyl, and like A(CO) groups.

Examples of peptides represented by the formula 1 wherein A is a bicyclic group represented by the foregoing formula 2 are the D-1,2,3,4-tetrahydroisoquinolin-1-ylcarbonyl (D-1-Tiq-Azt-Arg-H), D-1,2,3,4-tetrahydroisoquinolin-3-ylcarbonyl, D-perhydroisoquinolin-1-ylcarbonyl, and D-perhydroisiquinolin-3-ylcarbonyl derivatives of Azt-Arg-H depicted below,

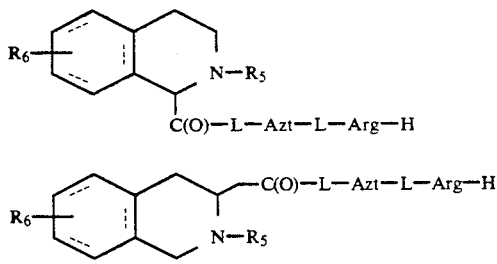

the 2,3-dihydroindole-3-ylcarbonyl group, the dihydroisoindole-1-ylcarbonyl (isoindoline-1-carbonyl) and the hexahydroisoindoline-1-carbonyl and the hexahydroisoindoline-3-carbonyl derivatives of Azt-Arg-H depicted below.

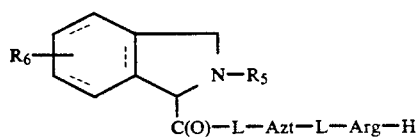

The terms $R_6$ and $R_5$ have the same meanings as defined hereinabove. $R_5$ is preferably hydrogen, and $R_6$ is preferably hydrogen, methoxy, ethoxy, chloro, or methyl.

The compounds represented by the formula 1 are prepared and used in the form of acid addition salts owing to the greater stability of the salt forms. Preferred salts are pharmaceutically acceptable non-toxic salts.

Pharmaceutically acceptable salts of peptides of the invention include the acid addition salts formed with inorganic acids and carboxylic acids. Examples of inorganic acids forming salts are the hydrohalic acids hydrochloric and hydrobromic; and the acids phosphoric acid and sulfuric acid. Carboxylic acid salts are formed with acids such as acetic, propionic, malonic, maleic, citric, succinic, malic, benzoic, fumaric, and like carboxylic acids. The acid addition salts are prepared in a conventional manner e.g. by neutralizing the free base form of the compound 1 with the acid. Preferred acid addition salts are sulfate and hydrochloride salts.

Preferred embodiments of the invention are compounds represented by the formula 1 wherein A is

where R is a phenyl group

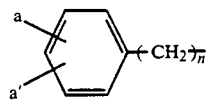

$R_1$ is hydrogen and B is an amino group —N($R_2$)($R_3$). Further preferred compounds are represented when $R_2$ is hydrogen and $R_3$ is an oxycarbonyl group $R_4$O—C(O)—. Also preferred are compounds wherein R is a naphthyl or substituted naphthyl group, and B and $R_1$ are as described in the above preferred group. Also preferred are compounds represented by 1 wherein B is an amino group —N($R_2$)($R_3$), $R_2$ is hydrogen and $R_3$ is a lower alkyl group especially methyl; $R_2$ is hydrogen and $R_3$ is trifluoracetyl; $R_1$ is hydrogen and R is a phenyl group shown above wherein n is 0 or 1.

An especially preferred embodiment of the invention comprises compounds of the formula 1 wherein A is a bicyclic group (2). Preferred compounds of this embodiment are represented by the formula 1 when A(C=O) of the formula 1 is the 1,2,3,4-tetrahydroisoquinolin-1-ylcarbonyl and 1,2,3,4-tetrahydroisoquinolin-3-ylcarbonyl. Another especially preferred embodiment comprises compounds represented by the formula 1 wherein A is (R)($R_1$)(B)-C-wherein R is a phenyl group as defined hereinabove with n=0 or 1; $R_1$ is methyl or ethyl and B is an amino group —N($R_2$)($R_3$).

The compounds represented by the formula 1 are prepared by known methods of peptide coupling. According to one such method, the cyclic lactam form of arginine (b) is prepared and coupled with an amino protected azetidine-2-carboxylic acid (a) as shown below to provide the dipeptide (c).

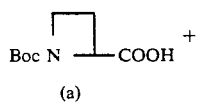

(a)

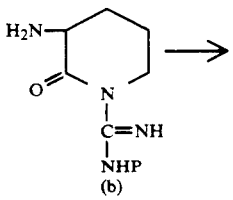

(b)

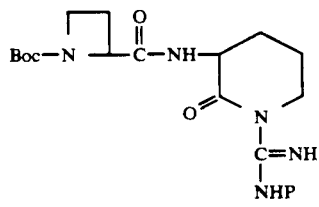

(c)

wherein P represents an amino protecting group such as the benzyl carbamate (Cbz) group, t-butyl carbamate (Boc), p-toluenesulfonyl, and the like. Preferably the amino protecting group used is removable by hydrogenation or treatment with mild acid (e.g. trifluoroacetic acid) or a strong acid (e.g. HF). Base labile protecting groups are not preferred. Examples of other suitable amino protecting groups are provided in "Protective Groups In Organic Synthesis", Second Edition, by Theodore W. Greene and Peter G. M. Wuts, Chapter 7, page 309-405 (1991), John Wiley & Sons, Inc., publishers incorporated herein by reference in its entirety. The Boc, or other suitable protecting group, is removed from the azetidine ring nitrogen which is then acylated with the desired acyl group or amino acid acyl group represented by A(C=O) in the formula 1 to provide the tripeptide (d) as shown below.

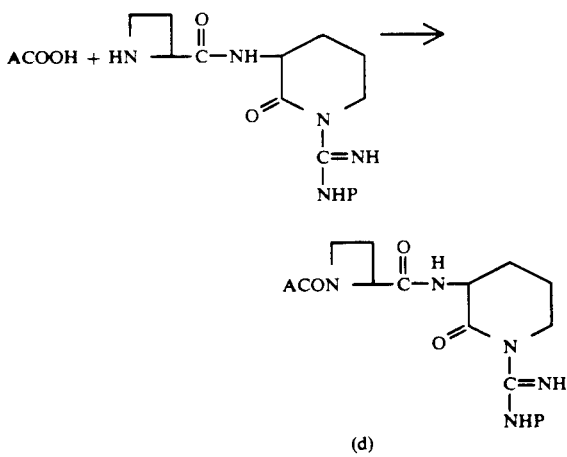

(d)

The coupled Arg(P) lactam product (d) is reduced with lithium aluminum hydride in an inert solvent to cleave the lactam ring and provide the tripeptide in the arginine aldehyde form represented by the formula A(C=O)—Azt—Arg(P)—H wherein Arg(P)—H represents amino protected arginine aldehyde.

The lactam form of arginine is obtained by intramolecular coupling of amino protected arginine [Arg-OH].

For example, Boc-Arg(Cbz)OH represented by the formula

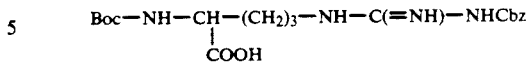

is first converted to an active ester form, such as an active mixed anhydride, with a chloroformate ester, e.g. ethyl chloroformate or isobutyl chloroformate. The ester formation is carried out in the presence of a tertiary amine such as N-methylmorpholine. Addition of a stronger tertiary amine base such as triethylamine effects the internal acylation to provide the lactam form of the diamino protected arginine as shown below.

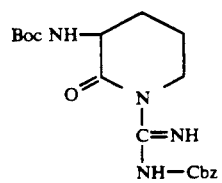

Prior to use in the coupling with the azetidine-2-carboxylic acid as shown in the above scheme, the Boc protecting group is selectively removed with trifluoroacetic acid to provide the requisite free amino group.

Alternatively, the compounds of the invention are prepared by coupling the ACOOH acid with 2-azetidine-carboxylic acid. The dipeptide is then coupled with the amino protected arginine in the lactam form prepared as described hereinabove. The tripeptide is then reduced to open the lactam ring and provide the amino protected arginal tripeptide as described above. Detailed exemplification of this sequence of coupling reactions is provided by Example 3 hereinafter.

The coupling of an ACOOH compound when A is an amino acid residue, is carried out by first protecting the amino group of the amino acid. Conventional amino protecting groups commonly used for temporary protection or blocking of the amino group are employed. Examples of such protecting groups include the alkoxy, alkenyloxy, cycloalkoxy, aralkoxy and aryloxycarbonyl groups such as ethoxycarbonyl, t-butyloxycarbonyl, cyclohexyloxycarbonyl, adamantyloxycarbonyl, trichloroethoxycarbonyl, benzyloxycarbonyl, diphenylmethoxycarbonyl, and like groups.

The compounds represented by the formula 1 wherein A is the group $(R)(R_1)(B)C-$ and B is an amino group $-N(R_2)(R_3)$ wherein $R_2$ is hydrogen and $R_3$ is lower alkyl are prepared with the corresponding compound wherein B is amino by using known alkylation methods. For example, N-methyl-D-phenylglycyl-L-azetidinyl-L-arginine aldehyde is prepared by reductive alkylation with formaldehyde. Substitution of acetaldehyde, propionaldehyde or butyraldehyde for formaldehyde provides the N-ethyl, N-n-propyl and, N-n-butyl alkyl derivatives. The reductive alkylation is carried out in an inert solvent in the presence of a hydrogenation catalyst e.g. 5% Pd/C, preferably under mild conditions of temperature and pressure. The reductive alkylation can be carried out on the amino acid A(C=O)-OH, e.g. phenylglycine or phenylalanine, and the N-alkyl derivative coupled with the L-azetidinyl-L-arginine lactam or, alternatively with L-azetidine-2-carboxylic acid and the dipeptide then coupled with the Arg (lactam).

Compounds represented by the formula 1 wherein A is (R)(R$_1$)(B)C—, and R is cyclohexadienyl or cyclohexenyl and B is an alkylamino group, —N(R$_2$)(R$_3$) can be prepared by reduction of the imine formed with a lower alkyl aldehyde with sodium cyanoborohydride. Likewise such N-alkylations can be carried out with a lower alkyl iodide and sodium hydride.

The compounds of the formula 1 wherein A is a bicyclic group (2) are prepared by the same coupling methods as above. For example the peptide of formula 1 wherein A represents the 1,2,3,4-tetrahydroisoquinolin-1-yl group (formula 2 Q = —CH$_2$CH$_2$—, Y = —CH—, R$_5$=R$_6$=H)

is obtained by acylation of the dipeptide D-1,2,3,4-tetrahydroisoquinolin-1-oyl-L-azetidine-2-carboxylic acid with L-Arg (lactam). Preferred derivatives of the carboxy group for coupling are active esters such as those formed by conventional means with hydroxybenzotrizole or 2,4,5-trichlorophenol. Other active derivatives that may be used include the acid halides such as the chloride or bromide, and the acid azide. The ring nitrogen of the tetrahydroisoquinoline (formula 2, R$_5$=H) is protected during the acylative coupling. For example an active ester of N-Boc-1,2,3-4-tetrahydro-1-carboxyisoquinoline formed with iso-butyl chloroformate is used in the acylation of the L-azetidine-2-carboxylic acid. The lactam group of the product is then converted to the aldehyde form as described above to provide the compound of the formula 1 namely, Boc-1,2,3,4-tetrahydroisoquinolin-1-ylcarbonyl-Azt-Arg-H.

The coupling reactions described above are carried out in the cold preferably at a temperature between about $-20°$ C. and about 15° C. The coupling reactions are carried out in an inert organic solvent such as dimethylformamide, dimethylacetamide, tetrahydrofuran, methylene chloride, chloroform, and like common solvents. Generally anhydrous conditions are used when, in the coupling reaction, an active ester of the acylating acid is used.

The compounds represented by the formula 1 wherein A is a group (R)(R$_1$)(B)C— wherein R$_1$ is methyl or ethyl are prepared by reacting the benzophenone imine derivative of a compound represented when B is an amino group —NH$_2$ with methyl iodide or ethyl iodide and potassium hydride in the presence of an 18-crown ether compound. For example, methyl phenylglycinate is reacted with benzophenone imine to form diphenylmethylimine of the glycinate represented by (C$_6$H$_5$)(H)([C$_6$H$_5$]$_2$C=N—)C—COOCH$_3$. The ester is then alkylated in an inert solvent with at least one equivalent of methyl iodide or ethyl iodide and potassium amide in the presence of an 18-crown-6 ether. The alkylated product represented by (C$_6$H$_5$—)(C̓H$_3$—)([C$_6$H$_5$]$_2$C=N—)C—COOCH$_3$ is then hydrolyzed to D-$\alpha$-methyl or $\alpha$-ethyl-phenylglycine in 6N hydrochloric acid.

The compounds of the invention are isolated in the form of acid addition salts. Salts of the compounds of formula 1 formed with acids such as those mentioned hereinabove are useful as pharmaceutically acceptable salts for administration of the antithrombotic agents and for preparation of formulations of these agents. Other acid addition salts may be prepared and used in the isolation and purification of the peptides. For example, the salts formed with the sulfonic acids such as methanesulfonic acid, n-butanesulfonic acid, p-toluenesulfonic acid and naphthalene sulfonic acid may be so used.

The preferred method for purifying the compounds represented by the formula 1, while at the same time preparing a desired stable salt form, is that described in copending application Ser. No. 790884 filed Nov. 12, 1991. According to the method, stable sulfates or hydrochlorides are provided by preparative purification over C$_{18}$ reversed-phase chromatography in which the aqueous component comprises sulfuric acid or hydrochloric acid at pH 2.5 and acetonitrile as the organic component. The pH of the acidic eluant is adjusted to between about pH4 and about 6 with an anion exchange resin in the hydroxyl form e.g. Bio-Rad AG-1X8. After adjustment of the pH, the solution of tripeptide sulfate or hydrochloride salt is lyophilized to provide the pure salt in dry powder form. In an example of the process, crude D-Phg-L-Azt-L-Arg-H sulfate is dissolved in water and the solution is loaded on Vydac C$_{18}$ RP-HPLC 5 cm X 50 cm column. A gradient of 2-10% B (A=0.01% H$_2$SO$_4$; B =acetonitrile) over 10 hours was used. Multiple fractions are collected and those containing product as determined by analytical RP-HPLC are pooled. The pH of the pooled fractions is adjusted to pH 4.0-4.5 with AG-1X8 resin in hydroxide form (Bio-Rad, 3300 Ragatta Blvd., Richmond, Calif. 94804). The solution is filtered and the filtrate is lyophilized to provide the pure D-,L-,L-,tripeptide in the form of the sulfate salt.

The compounds provided by the invention (formula 1) inhibit the action of thrombin in man and animals. The inhibition of thrombin is demonstrated by in vitro inhibition of the amidase activity of thrombin as measured in an assay in which thrombin hydrolyzes the chromogenic substrate, N-benzoyl-D-phenylalanyl-L-valyl-L-arginyl-p-nitroanilide.

The assay was carried out in 50 $\mu$l buffer (0.03M Tris, 0.15M NaCl, pH 7.4) with 25 $\mu$l of thrombin solution (0.21 mg/ml of thrombostat powder in 0.06M Tris, 0.3M NaCl, pH 7.4) and 150 $\mu$l of an aqueous solution of the chromogenic substrate at a concentration of 0.25 mg/ml. Solutions of test compound (25 $\mu$l) at various concentrations were added. Rates of hydrolysis of the substrate were measured by monitoring the reactions at 405 nm for the release of p-nitroaniline. Standard curves were constructed by plotting free thrombin concentration against hydrolysis rate. The hydrolysis rates observed with test compounds are then converted to "free thrombin" values in the respective assays by use of the standard curves. The bound thrombin (bound to test compound) was calculated by subtracting the amount of free thrombin observed in each assay from the known initial amount of thrombin used in the assay. The amount of free inhibitor in each assay was calculated by subtracting the number of moles of bound thrombin from the number of moles of added inhibitor (test compound).

The Kass value is the hypothetical equilibrium constant for the reaction between thrombin and the test compound (I).

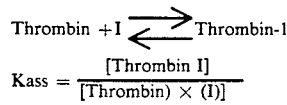

Kass was calculated for a range of concentrations of test compounds and the mean value is reported in units of liter per mole.

The thrombin inhibiting activity of the compounds of the invention is exemplified by the Kass values of $6.5 \times 10^7$ and $14.9 \times 10^7$ (1/mole) obtained in the above described assay with Boc-D-Phe-L-Azt-L-Arg-H and Boc-D-Phg-L-Azt-L-Arg-H respectively.

Table 1 which follows lists the Kass values obtained with the indicated compound represented by the formula 1.

TABLE 1

Thrombin Inhibition Levels

| Compound[1] | Kass × $10^6$(1/mole) |
|---|---|
| TFA—D—Phg(α-Et)—Azt—Arg—H | 226 |
| Boc—D—Phg—Azt—Arg—H | 149 |
| TFA—D—Phg(α-Me)—Azt—Arg—H | 127 |
| Boc—D—Phe—Azt—Arg—H | 65 |
| Ac—D—Phg(α-CH$_3$)—Azt—Arg—H | 70 |
| Boc—D—Phg(α-CH$_3$)—Azt—Arg—H | 61 |
| D-3-Tiq—Azt—Arg—H | 35 |
| DL-1-Tiq—Azt—Arg—H | 27 |
| Ac—Phg(α-CH$_3$)—Azt—Arg—H | 15 |
| Boc—DL—Phg(α-CH$_3$)—Azt—Arg—H | 11 |

D—Phg = phenylglycyl
Azt = azetidinyl
3-Tiq = 1,2,3,4-tetrahydroisoquinolin-3-carbonyl
1-Tiq = 1,2,3,4-tetrahydroisoquinolin-1-carbonyl
Ac = acetyl
TFA = trifluoroacetyl The compounds of the invention inhibit clot formation without appreciable interference with the bodies natural clot lysing ability e.g. the compounds have a low inhibitory effect on fibrinolysis.

The invention in one of its aspects provides a method for inhibiting the formation of blood clots in man and animals which comprises administering to said man or animal an effective clot inhibiting non-toxic dose of a compound represented by the formula 1. The anticoagulant compound is administered orally, parenterally e.g. by intravenous infusion (iv), intramuscular injection (im) or subcutaneously (sc). Depending upon circumstances such as the condition of the host, e.g., the host's need for acute or chronic care, the route of administration may be p.O. or i.v.

An effective clot inhibiting dose is between about 5 mg and about 1000 mg. The dose regimen may vary e.g. for prophylactic use a single daily dose may be administered or multiple doses such as 3 or 5 times daily may be appropriate. In critical care situations a compound of the invention is administered by iv infusion at a rate between about 0.1 mg/kg/h and about 50 mg/kg/h and preferably between about 1.0 mg/kg/h and about 20 mg/kg/h.

The method of this invention also is practiced in conjunction with a clot lysing agent e.g. tissue plasminogen activator (tPA), modified tPA, streptokinase or urokinase. In cases when clot formation has occurred and an artery or vein is blocked, either partially or totally, a clot lysing agent is usually employed. A compound of the invention can be administered along with the lysing agent or subsequent to its use to prevent the reoccurrence of clot formation.

In carrying out the method the use of a preferred compound of the invention is desirable. For example use is made of a preferred compound such as described hereinabove. Especially preferred are N-Boc-D-phenylglycyl-L-azetidinyl-L-arginine aldehyde and N-methyl-D-phenylglycyl-L-azetidinyl-L-arginine aldehyde.

The invention also provides pharmaceutical formulations for use in the above described therapeutic method. Pharmaceutical formulations of the invention comprise an effective clot inhibitory amount of a compound represented by the formula 1 and a pharmaceutically acceptable carrier. For oral administration the antithrombotic compound is formulated in gelatin capsules or tablets which may contain excipients such as binders, lubricants, disintegration agents and the like. For parenteral administration the antithrombotic is formulated in a pharmaceutically acceptable diluent e.g. physiological saline (0.9%), 5% dextrose, Ringer's solution and the like.

The antithrombotic compound of the invention can be formulated in unit dosage formulations comprising a dose between about 1 mg and about 1000 mg. Preferably the compound is in the form of a pharmaceutically acceptable salt such as for example the sulfate salt, acetate salt or a phosphate salt. An example of a unit dosage formulation comprises 5 mg of N-Boc-D-phenylglycyl-L-azetidinyl-L-arginine aldehyde sulfate salt in a 10 ml sterile glass ampoule. Another example of a unit dosage formulation comprises about 10 mg of N-methyl-D-phenylalanyl-L-azetidinyl-L-arginine aldehyde sulfate in 20 ml of isotonic saline contained in a sterile ampoule.

The following Examples are provided to further describe the invention and are not to be construed as limitations thereof.

The R$_f$ values in the following examples were determined by silica gel thin layer chromatography using Kieselgel 60F-254 (Merck, Darmstadt) in the following solvent systems:

(A) chloroform-methanol-acetic acid, 135:15:1, v:v:v
(B) ethyl acetate-acetic acid-absolute ethanol, 90:10:10, v:v:v
(C) chloroform-methanol-acetic acid, 90:30:5, v:v:v The analytical HPLC method used in the examples for monitoring chromatographic fractions, determination of retention times, and purity of product was as follows:

Waters 600E using a Vydac C$_{18}$ reversed-phase column of 0.46 cm × 10 cm. Monitoring was done on a Pharmacia UV-M at 214 nM using a gradient of either A =0.01M ammonium acetate or B=acetonitrile. Pharmacia, Inc., 800 Centennial Ave., Piscataway, N.J. 08854.

The abbreviations used in the examples have the following meanings.

Amino acids: Arg=arginine, Azt=azetidine, Pro=proline, Phg=phenylglycine, 1-Tiq =1,2,3,4-tetrahydroisoquinolin-1-carbonyl
Boc=t-butyloxycarbonyl
Bzl=benzyl
Cbz=benzyloxycarbonyl
DCC=dicyclohexylcarbodiimide
DMF=dimethylformamide
DMSO=dimethylsulfoxide
FAB-MS=fast atom bombardment mass spectrum
FD-MS=field desorption mass spectrum
THF=tetrahydrofuran
TLC=thin layer chromatography
EtOAc=ethyl acetate
n-BuOH=n-butyl alcohol

EXAMPLE 1

N-(N-t-Butyloxycarbonyl-D-phenylglycyl)-L-azetidinyl-L-arginine aldehyde diacetate 1) t-Boc and Cbz diprotected arginine N-(t-butyloxycarbonyl) arginine hydrochloride [Boc-Arg (HCl)-OH], (82.1 g, 250 mmole) was dissolved in 5N sodium hydroxide (240 ml) in a 3-neck round bottom flask. The solution was cooled to −5° C. and benzyl chloroformate (143 ml, 1.0 mole, 4 e.g.) was added dropwise over 55 min. while the pH was maintained at 13.2-13.5 with 5N sodium hydroxide (25 ml). The reaction mixture was stirred for 1 h at −5° C. after addition was complete and was diluted with 100 ml of water. Diethylether (500 ml) were added and the aqueous layer was separated and extracted twice with 500 ml portion of diethylether. The aqueous layer was acidified to pH 3.0 with 3N sulfuric acid (560 ml) and extracted with 550 ml of ethyl acetate. The aqueous layer was extracted with ethyl acetate and the extracts were combined, washed with water, dried over magnesium sulfate, and evaporated to dryness in vacuo to give 66.1 g of the diprotected arginine, Boc-Arg(Cbz)-OH (1).

TLC $R_f(C)$ 0.43
FD-MS 408 (M+)
$^1$HNMR (CDCl$_3$) δ1.42 (s 9H) 1.61-1.91 (m 4H) 3.23−3.41 (m, 2H), 4.17 (d, 1H), 5.21 (s, 2H), 5.62 (d, 1H), 7.30-7.42 (m, 6H), 8.37 (m, 1H).

2) Boc-Arg(Z)-Lactam

The diprotected arginine prepared as described in part 1 above (66.0 g, 0.162 mole) was dissolved in 230 ml of dry THF and the solution was cooled to −10° C. in an ice-acetone bath. To the solution was added triethylamine (23.5 ml, 1.05 eq) followed by isobutylchloroformate (22.5 ml, 1.05 eq) and the mixture was stirred for 5 min at −10° C. Next, N-methylmorpholine (18.7 ml, 1.05 eq) was added and the reaction mixture was stirred 1 h at −10° C. and 1 h at room temperature. The reaction mixture was poured into one liter of ice-water and the precipitate which formed was filtered, washed with cold water and dried in vacuo. The product, Boc-Arg(Z)-lactam (2) was crystallized from ethyl acetate giving 38.05 g (60% yield)

TLC $R_f(A)$ 0.77
FD-MS 391 (MH+)
$^1$HNMR (CDCl$_3$) δ 1.48 (s, 9H), 1.78-1.98 (m, 2H), 2.50 (m, 1H), 3.41 (m, 1H), 4.43 (m, 1H), 4.90 (m, 1H), 5.16 (s, 2H), 5.27 (m, 1H), 7.28-7.45 (m, 6H), 9.41 (m, 1H), 9.68 (m, 1H).

3) Arg (Z)-Lactam trifluoroacetate salt

The Boc protected Arg lactam (2) (38.0 g, 0.097 mole) prepared as described above was treated with trifluoroacetic acid (200 ml) and 20 ml of anisole with stirring at 0° C. for 1 hour. The reaction mixture was concentrated under vacuum without heating and 400 ml of diethylether was added to the concentrate. The solid was filtered, washed with ether and dried in vacuo to give 40.5 . g of 3.

TLC $R_f(C)$ 0.29
FD-MS 291 (MH+)

4) N-(t-Butyloxycarbonyl) azetidine-2-carboxylic acid Boc-Azt-OH

L-Azetidine-2-carboxylic acid (5 g, 0.0495 mole) was dissolved in 50 ml of t-butyl alcohol containing 50 ml of 2N sodium hydroxide (0.099 mole). Di-t-butyl-dicarbonate (12.9 g, 0.0594 mole) was added to the solution and the reaction mixture was stirred overnight at room temperature. The reaction mixture was diluted with water and diethylether and the aqueous layer separated. The aqueous layer was acidified to pH 2.3 with 3N HCl and then extracted with ethyl acetate. The extract was dried over MgSO$_4$ and concentrated by evaporation in vacuo to an oil. The oil was crystallized from (C$_2$H$_5$)$_2$O/petroleum ether to give 8.6 g of 4 (87% yield).

FAB-MS 202 (MH+)
$[\alpha]_D$=−120° C.=0.5 CH$_3$OH
Elemental Analysis for C$_9$H$_{15}$NO$_4$
Theory: C, 53.72; H, 7.51; N, 6.96
Found: C, 53.62; H, 7.63; N, 6.83

5) Boc-Azt-Arg(Z)-Lactam

Boc-Azt-OH (4) (1.51 g, 7.5 mmole) was dissolved in 20 ml of DMF, the solution cooled to −15° C. and 0.83 ml (7.5 mmole) of N-methylmorpholine was added first followed by isobutylchloroformate (0.93 ml, 7.5 mmole). The solution was stirred at −15° C. for two minutes.

In a separate vessel, Arg(Z)-Lactam trifluoroacetate salt (3) (3.03 g, 7.5 mmole) was dissolved in 10 ml of DMF, the solution cooled to 0° C. and N-methylmorpholine (0.83 ml, 7.5 mmole) was added to the solution. The solution was stirred at 0° C. for two minutes and then mixed with the solution obtained above. The reaction mixture was stirred for 2 h at −15° C. and then slowly warmed to room temperature overnight. A 5% solution of sodium bicarbonate (5 ml) was added and the reaction mixture diluted with 175 ml of diethylether and 150 ml of water. The organic layer was separated, washed with 5% NaHCO$_3$, water, 1.5N citric acid and with water. The washed layer was dried over MgSO$_4$ and concentrated by evaporation under vacuum to yield 3.5 g of 5 as an amorphous solid, (99% yield).

TLC $R_f(A)$ 0.71
FAB-MS 474 (MH+)
$^1$HNMR (CDCl$_3$) δ 1.45 (s, 9H), 1.55-1.65 (m, 2H), 1.80-2.00 (m, 2H), 2.40-2.60 (m, 3H), 3.45 (m, 1H), 3.80 (q, 1H), 3.95 (q, 1H), 4.68 (m, 1H), 4.90 (m, 1H), 5.15 (s, 2H), 7.30-7.42 (m, 5H)

6) Azt-Arg(Z)Lactam trifluoroacetate

The Boc-Azt-Arg(Z)-Lactam (5) (3.4 g, 7.2 mmole) was treated with 25 ml of trifluoroacetic acid and 5 ml of anisole with stirring for 30 min at 0° C. The reaction mixture was concentrated by evaporation under vacuum without heating and the concentrate treated with 100 ml of diethylether. The solid was filtered, washed with diethylether and dried under vacuum to yield 3.5 g of 6 (100% yield).

FD-MS 374 (MH+)

7) Boc-D-Phg-Azt-Arg(Z)lactam

Boc-D-Phenylglycine (0.88 g 3.5 mmole) and Azt-Arg (Z) lactam trifluoroacetate salt (6) (1.71 g, 3.5 mmole) were dissolved in 10 ml of DMF and the solution cooled to 0° C. To the solution was added N,N-diisopropylethylamine (0.73 ml, 4.2 mmole) followed by 1-hydroxybenztriazole hydrate (0.47 g, 3.5 mmole) and dicyclohexycarbodiimide (0.72 g, 3.5 mmole). The reaction mixture was stirred at 0° C. for 4 h and for 3 days at room temperature. The mixture was filtered and the filtrate dissolved in 200 ml of ethyl acetate and 100 ml of 5% NaHCO$_3$. The organic layer was separated and washed with water, 1.5N citric acid (100 ml), H$_2$O (150 ml) and dried over MgSO$_4$. The layer was concentrated to dryness by evaporation under vacuum to yield 1.2 g of 7 as a solid (57% yield)

TLC $R_f(A)$ 0.65

FAB-MS 607 (MH+)

8) Boc-D-Phg-L-Azt-L-Arg-(Z)-H

Boc-D-Phg-L-Azt-L-Arg (Z)-Lactam (7) (1.16 g, 1.91 mole was dissolved in 100 ml of dry THF. The solution was cooled to −15° C. under $N_2$ and lithium aluminum hydride 1M in THF (1 9 ml, 1.9 mmole), was added dropwise over 3 min. The reaction mixture was warmed to 0° C. and stirred for 1 h. A solution of 5 ml of THF and 5 ml of 0.5N $H_2SO_4$ was added slowly by dropwise addition over 10 min. The reaction mixture was diluted with 100 ml of ethyl acetate and 50 ml of water and the organic layer separated and dried over $MgSO_4$. The dried layer was concentrated under vacuum to yield 0.97 g (84% yield).

FAB-MS 609 (MH+)

The title compound was obtained with 9 as follows. To a solution of 9 (0.95 g, 1.56 mmole) in 120 ml of THF and 30 ml of water was added acetic acid (0.19 ml, 2 eq) and 0.5 g of 10% palladium on carbon catalyst. Nitrogen was bubbled through the suspension through a gas dispersion tube for 5 min. followed by hydrogen for 4 h and thereafter nitrogen again for 5 min. The catalyst was filtered using a filter pad. The filtrate was concentrated under vacuum to a volume of 20 ml and the concentrate lyophilized to yield 0.822 of crude title peptide as a solid.

The title compound was chromatographed on a 5×25 cm C-18 reversed phase HPLC column (Vydac C-18, Separation Group, 17434 Mojave St., Hesperia, Calif. 92345) using of 10-50% acetonitrile/0.01M ammonium acetate gradient over 9 h. Multiple fractions were collected and pooled on the basis of analytical reversed phase HPLC profile. The pooled fraction were lyophilized to yield 0.303 g (41% yield) of the purified title compound.

FAB-MS 475 (MH+)

$[\alpha]_D = -146.2°$ C.=0.5 in 1M acetic acid

Retention Time: RP-HPLC:5 to 50% acetonitrile over 60 min.=48.5 min

EXAMPLE 2

N-(N-t-Butyloxycarbonyl)-D-phenylalanyl-L-azetidinyl-4-arginine aldehyde diacetate By using the procedures, reaction conditions and reagents employed as described in Example 1 and by substituting D-phenylalanine for the D-phenylglycine of Example 1. The title compound was obtained.

FAB-MS 489 (MH+)

Retention Time: 40.9 min.

EXAMPLE 3

DL-1,2,3,4-tetrahydroisoquinolin-1-oyl-L-azetidinyl-L-arginine aldehyde sulfate

1) DL-1,2,3,4-tetrahydroisoquinolin-1-carboxylic acid. A solution of isoquinoline-1-carboxylic acid (12.5 g, 0.072 mole) in 185 ml of glacial acetic acid was hydrogenated at room temperature for 24 hours over 2 g of platinum oxide catalyst under 60 psi hydrogen pressure in a Parr hydrogenation apparatus. The reaction mixture was filteed through a filter pad (celite) and the filtrate evaporated to dryness in vacuo. The solid residue of product was triturated with water, filtered and dried to give 8 g (63% yield) of pure 1.

FD-MS 178 (MH+)

$^1$HNMR(DMSO) δ 2.80–3.00 (m, 3H), 3.10–3.20 (m, 1H), 3.30–3.40 (m, 2H), 7.05–7.25 (m, 4H), 7.65–7.75 (m, 1H).

2) t-Butyloxycarbonyl-DL-1,2,3,4-tetrahydroisoquinolin-1-carboxylic acid dicyclohexylamine salt. (Boc-DL-Tiq DCHA)

To a solution of 1,2,3,4-tetrahydroisoquinolin-1-carboxylic acid (1) (7.08 g, 0.040 mole) in 2N sodium alcohol and di-t-butyl dicarbonate (10.5 g, 0.048 mole). After about 24 h at room temperature the bulk of the t-butyl alcohol was evaporated from the reaction mixture and the resulting aqueous phase was washed once with diethyl ether. The aqueous layer was acidified to pH 2.0 with 2N HCl and extracted with ethyl acetate. The extract was dried over $MgSO_4$ and evaporated to dryness in vacuo. The residue (oil) was dissolved in diethyl ether and dicyclohexylamine, DCHA, (7.9 ml, 0.040 mole) was added to the solution. The solution was allowed to stand for 4 hours at 4° C. and the salt which had precipitated was filtered, washed with diethyl ether and dried under vacuum to give 15.7 g (86% yield) of the pure DCHA salt 2.

FD-MS 459 (MH+)

Elemental analysis for $C_{27}H_{42}N_2O_4$.

Theory: C,70.71; H, 9.23; N, 6.11.

Found: C, 71.07; H, 9.37; N, 5.87.

3) t-Butyloxycarbonyl-DL-1,2,3,4-tetrahydroisoquinolin-1-oyl-azetidine-2-carboxylic acid. (Boc-DL-1-Tiq-Azt-OH).

The DCHA salt(2) (13.7 g, 30 mmole) was suspended in 200 ml of ethyl acetate and the suspension washed with 1.5N citric acid and with water and was dried over Mg $SO_4$. The suspension was evaporated to dryness under vacuum and the oil residue was dissolved in 100 ml of ethyl acetate. The solution was cooled to 0° C. and 2,4,5-trichlorophenol (5.91 g 30 mmole) was added followed by DCC (6.18 g, 30 mmole). The reaction mixture was stirred for 5 minutes at 0° C. and then warmed to room temperature and stirred for 1.5 h. The reaction mixture was cooled to 0° C., the precipitate filtered and the mother liquor evaporated to dryness in vacuo. The oil residue was dissolved in 80 ml of pyridine and 2-azetidine-2-carboxylic acid (3.0 g, 30 mmole) and 4.2 ml (30 mmole) of triethylamine were added to the solution. The reaction mixture was stirred for 48 h at room temperature and was evaporated to dryness under vacuum. The residue was dissolved in ethyl acetate/water and the pH of the solution was adjusted to 9.5 with 2N sodium hydroxide. The aqueous layer was separated, acidified to pH 2.0 with 2N HCl and then extracted with ethyl acetate. The extract was dried over $MgSO_4$ and evaporated to dryness in vacuo to give 10 g of 3.

The product (3) was dissolved in chloroform:hexane (1:1,v:v) and the solution appliedc to a silica gel column equilibrated in hexane in a Water's Prep 500A. The product (3) was eluted with a gradient of increasing concentrations of ethyl acetate. Fractions were collected and the product isolated based on TLC profile. Fractions wer combined and evaporated to dryness to give 4.8 g (44% yield) of pure 3.

TLC Rf (A) 0.35

FAB-MS 361 (MH+)

$[\alpha]D = -20.6°$ C.=0.5 $CH_3OH$ 4) t-Butyloxycarbonyl-DL-1,2,3,4-tetrahydro-1-isoquinolinoyl-L-azetidinyl-L-arginine(Cbz)lactam(4) (Boc-DL-1-Tiq-Azt-Arg(Z)-Lactam).

In a first flask Boc-DL-1-Tiq-Azt (3) (5.3 g, 15 mmole) was dissolved in 50 ml of DMF and the solution cooled to −15° C. N-Methylmorpholine (1.65 ml, 15 mmole) and the reaction mixture was stirred at −15° C. for two minutes.

In a second flask Arg(Z)-Lactam as the trifluoroacelate salt (TFA) (6.06 g, 15 mmole) was dissolved in 20 ml of DMF and the solution cooled to 0° C. N-Methylmorpholine (1.98 ml, 19 mmole) was added to the cold solution which was stirred for 2 min at 0° C. Then the contents of the second flask were poured into the first flask and the reaction mixture was stirred at −15° C. for 3 h. The mixture was slowly warmed to room temperature overnight and was then evaporated to an oil in vacuo. Ethyl acetate (175 ml) and 1N NaHCO$_3$ (100 ml) were added to the oil. The organic layer was separated, washed with water, 1.5N citric acid, and again with water. The solution was dried over Mg SO$_4$ and evaporated to dryness under vacuum to give 6.9 g (73% yield) of 4,Boc-DL-1-Tiq-Azt(Z)-Lactam as an amorphorous solid.

TLC R$_f$(A) 0.64
FAB-MS 633 (MH+)
[α]D −62.5° C. C=0.5 CHCl$_3$

5) Boc-DL-1-Tiq-Azt-Arg(Z)-H(5)

A solution of Boc-DL-1-Tiq-Azt-Arg(Z)-Lactam(4) (6.3g, 10 mmole) in 85 ml if dry THF was cooled in an atmosphere of nitrogen to −15° C. and lithium aluminum hydride, 1M in THF (10 ml, 10 mmole) was added dropwise over 30 min. After addition of the hydride was complete, the reaction mixture was stirred for 30 min. at −15° C. Next, a solution of 10 ml of THF and 3.0 ml of 0.5N H$_2$SO$_4$ was added dropwise to the reaction mixture over 5 min. The mixture was diluted with 200 ml of ethyl acetate and 200 ml of water, the organic layer separated, dried over Mg SO$_4$ and evaporated to dryness under vacuum to give 6.0 g (95% yield) of 5 as an amorphous solid.

TLC R$_f$(A) 0.18.

6) DL-1-Tiq-Azt-Arg-H sulfate

To a solution of (5) (5.9 g, 9.3 mmole) in 60 ml of THF and 30 ml of water were added 10 ml of 1N H$_2$SO$_4$ and 2.0 g of 5% Pd/c catalyst. Nitrogen was bubbled through the suspension with a gas dispersion tube for 5 minutes followed by hydrogen for 1.5 h and again with nitrogen for 5 min. The catalyst was filtered and the pH of the filtrate was adjusted to pH 4.0 with Bio-Rad AG1-X8 resin (hydroxide form). The resin was filtered and the filtrate freeze dried to give 4.5 g of dry solid. The solid was treated for 10 minutes at 0° C. with 20 ml of trifluoroacetic acid and 5 ml of anisole. The reaction mixture was stirred for 10 min and then evaporated without heat. Diethyl ether (100 ml) was added to the concentrate and the precipitate which formed was collected and dried to give 4.8 g of the crude product. The crude product (4.8 g) was dissolved in 0.01% H$_2$SO$_4$ and applied to two 5×25 cm Vydac C$_{18}$ resin columns connected in series. A gradient of increasing concentration of acetonitrile (2% to 25%) was used to elute the peptide salt from the column. Fractions were collected and pooled on the basis of analytical RP-HPLC described hereinabove. The pH of the pooled fractions were adjusted to pH 4.0 using AG1-X8 resin (Bio Rad anion exchange resin, 50–100 mesh) in hydroxide form. The resin was filtered and the filtrate lyophilized to give 1.36 g (30% yield) of the purified title sulfate salt.

FAB-MS 401 (MH+)
HPLC Retention Time: 23.1 min

EXAMPLE 4

D-1,2,3,4-Tetrahydroisoquinolin-3-oyl-L-azetidin-2-oyl-L-arginine aldehyde sulfate. (D-3-Tiq-Azt-Arg-H)

The title compound was prepared by substituting 1,2,3,4-tetrahydroisoquinolin-3-carboxylic acid for 1,2,3,4-tettrahydroisoquinoline-1-carboxylic acid in the procedure of Example 3.

FAB-MS 401(MH+)
Retention Time: 18.5 min

EXAMPLES 5–8

Table 2 lists the mass spectrum and HPLC retention times for representative compounds of the invention wherein A is (4)(R$_1$)(B)C- and R$_1$ is methyl that were prepared by the general coupling methods of the foregoing Examples.

TABLE 2

| Ex No. | Compound[1] | FAB-MS(MH+) | Retention Time(min)[2] |
|---|---|---|---|
| 5 | N—Acetyl—D—Phg(α-CH$_3$)—Azt—Arg—H | 431 | 20.4 |
| 6 | N—Boc—D—Phg(α-CH$_3$)—Azt—Arg—H | 489 | 36.3 |
| 7 | N—Acetyl—DL—Phg(α-CH$_3$)—Azt—Arg—H | 431 | 21.6 |
| 8 | N—Boc—DL—Phg(α-CH$_3$)—Azt—Arg—H | 489 | 39.0 |

[1]sulfate salt
[2]Obtained via the Analytical RP-HPLC method described hereinabove.

EXAMPLE 9

N-[N-trifluoracetyl-D-(α-methyl)phenylglycyl)-L-azetidinyl-L-arginine aldehyde hydrochloride TFA—D—Phg(αMe)—Azt—Arg—H.HCl The procedures of steps 1 and 2 of Example 1 were followed to provide Boc-Arg(Z)-Lactam.

3) HCl-Arg(Z)-Lactam

A solution of HCl(g) saturated in EtOAc(7.2 L) was added dropwise over 30 min. to a solution of Boc-Arg(Z)-Lactam (2) (641 g, 1.64 mol) dissolved in CH$_2$CL$_2$(3L) at −10° C. temperature over 3 h. Diethyl ether (12 L) was added and the precipitate was filtered, washed with diethyl ether, and dried in vacuo to give 580 g of the title compound (108% of theory): TLC R$_f$ (C) 0.29; FD-MS 291 (MH+).

4) Methyl-Nαdiphenylmethylene-DL-phenylglycinate

Benzophenone imine (53.8 g, 297 mmol) was dissolved in methylene chloride (500 mL) and stirred at room temperature. To the solution was added DL-phenylglycine methylester hydrochloride (59.9 g, 297 mmol) and the reaction stirred at room temperature for 48 h. The reaction mixture was washed 3 times with water (200 mL). The organic layer was separated, dried (MgSO$_4$), and the filtrate was concentrated in vacuo to give a clear oil. The oil was crystallized from pentane to give the title compound (98.5 g, 100%) FAB-MS 330 (MH+); elemental analysis (calcd) C$_{22}$H$_{19}$NO$_2$:

C,80.22; H,5.81; N,4.25. Found; C,80.50, H, 5.93, N, 4.14

5) Methyl-Nα-diphenylmethylene-DL-(α-methyl)-phenylglycinate

A solution of methyl-Nα-diphenylmethylene-DL-phenylglycinate (4) (14.8 g, 44.8 mmol) in anhydrous THF (200 mL) was added dropwise to a mixture of 18-crown-6 (11.8 g, 44.8 mmol), potassium hydride (11.2 g, 67.3 mmol), THF (100 mL), and stirred under a nitrogen atmosphere. To the reaction was added methyl iodide (6.0 mL, 89.7 mmol) dissolved in THF (20 mL) dropwise. The reaction was stirred for an additional 1.5 h after addition at room temperature. To the reaction mixture was added a solution containing glacial HOAc (7.0 mL), water (25 mL), and THF (30 mL) dropwise. The reaction mixture was diluted with ethyl acetate and water. The organic layer was separated, washed 3 times with water, and dried ($MgSO_4$). The filtrate was concentrated in vacuo to give an oil. The crude oil was crystallized from hexane to give the title compound (10.2 g, 66%) FAB-MS 344 ($MH^+$); elemental analysis (calcd) $C_{23}H_{21}NO_2$: C,80.44; H, 6.16; N, 408. Found: C, 80.40, H, 6.26, N, 4.03.

6) DL-(α-methyl)phenylglycine

A solution of methyl-Nα-diphenylmethylene-DL-(α-methyl)phenylglycinate (5) (72.4 g, 211 mmol) in 5N HCl (400 mL) was refluxed (24 h). The solution was cooled to room temperature, filtered and the pH of the filtrate adjusted to 5.8 with dilute $NH_4OH$ solution. The aqueous solution was concentrated in vacuo until crystallization began. The reaction mixture was stored overnight at 5° C. and the precipitate filtered to give the title compound (22 g, 63%) FAB-MS 166 ($MH^+$)

7) Trifluoroacetyl-DL-(α-methyl)phenylglycine

To a solution of DL-(α-methyl)phenylglycine (6) (21.9 g, 133 mmol) in trifluoroacetic acid (250 mL) was added trifluoroacetic anhydride (33.5 g, 159 mmol) and the reaction mixture refluxed (2 h). The reaction mixture was concentrated in vacuo to an oil and diluted with EtOAc/water. The organic layer was separated and washed 3 times with water, dried ($MgSO_4$), and the filtrate concentrated in vacuo to give the title compound (25.3 g, 73%) as a white solid FAB-MS 262 ($MH^+$).

8) Trifluoroacetyl-DL-(α-methyl)phenylglycine-Azt-OH

Trifluoroacetyl-DL-(α-methyl)phenylglycine (7) (8.0 g, 31 mmol) was dissolved in EtOAc (80 mL) and the solution cooled to 0° C. To the solution was added 2,4,5-trichlorophenol (6.1 g, 31 mmol) and dicyclohexylcarbodiimide (6.3 g, 31 mmol). The reaction was stirred for 1 h at 0° C. and 1.5 h at room temperature. The precipitate was filtered and the filtrate concentrated in vacuo to an oil. The oil was dissolved in pyridine (60 mL), L-azetidine-2-carboxylic acid (3.1 g, 31 mmol), and triethylamine (4.3 mL, 31 mmol) was added. The reaction was stirred at room temperature (24 h). The reaction solvent was removed in vacuo to an oil. The oil was dissolved in water (100mL), diethyl ether (50mL) and the pH adjusted to 9.0 with 2N NaOH. The aqueous layer was extracted 2 times with diethyl ether. The aqueous layer was separated, EtOAc (150 mL) was added, and the pH of the solution adjusted to 3.0 with 3N HCl. The organic layer was separated, dried ($MgSO_4$), and the filtrate evaporated in vacuo to an amorphous solid (9.3 g, 88%); FD-MS 345 ($MH^+$); $[\alpha]_D = -80°$ (C=0.5/$CHCl_3$).

9) Trifluoroacetyl-D-(α-methyl)phenylglycine-Azt-Arg(Z)-Lactam

In flask 1 Trifluoroacetyl-DL-(α-methyl)-phenylglycine-Azt-OH (8) (6.7 g, 19.9 mmol) was dissolved in DMF (50 mL), cooled to −15° C. and N-methylmorpholine (2.5 mL, 21.9 mmol) was added followed by isobutylchloroformate (2.6 mL, 19.9 mmol). The reaction mixture was stirred at −15° C. for 2 min.

In flask 2 HCl.Arg(Z)-Lactam (3) (6.5 g, 19.9 mmol) was dissolved in DMF (40 mL), cooled to 0° C., and diisopropylethylamine (7.0 mL, 39.9 mmol) was added. The reaction mixture was stirred at 0° C. for 2 min.

The contents of flask 2 were added to flask 1 in one portion and the reaction mixture was stirred for 4 h at −15° C. The reaction mixture was slowly warmed to room temperature over 24 h period. To the reaction mixture was added 1N $NaHCO_3$ (18 mL) and stirred at room temperature for 3 min. The reaction was diluted with EtOAc (200 mL), water (100 mL), and the organic layer was separated, washed with 1N $NaHCO_3$, water and 0.1N HCl. The organic layer was dried ($MgSO_4$), and evaporated to an amorphous solid of crude title compound (11.5 g, 93%). The crude solid (11.5 g) was applied to two silica gel columns in a Water's Prep 500 A chromatography apparatus. A gradient system consisting of (A) $CH_2Cl_2$ and (B) EtOAc was used to elute the pure compound. The gradient used was an increasing concentration of EtOAc from 0% to 20%. Fractions were collected and pooled on the basis of TLC profile. The combined fractions were concentrated in vacuo to give the title compound as an amorphous solid (3.02 g, 25%): TLC $R_f$ (D) 0.45;FAB-MS 617 ($MH^+$);$[\alpha]_D = -95.9°$ (C=0.5/$CHCl_3$).

10) Trifluoroacetyl-D-(α-methyl)phenylglycine-Azt-Arg(Z)-H

Trifluoroacetyl-D-(α-methyl)phenylglycine-Azt-Arg(Z)-Lactam (9) (2.9 g, 4.8 mmol) was dissolved in anhydrous THF (60 mL) and placed in a flask under nitrogen atmosphere. The reaction mixture was cooled to −70° C. To the reaction mixture was added lithium aluminum hydride 1M in THF (5.0 mL, 5.0 mmol) and diluted with THF (10 mL) dropwise over 5 min period. The reaction mixture was stirred at −70° C. for 30 min and a solution of 5 mL of THF and 5 mL of 0.5N $H_2SO_4$ was added dropwise slowly. The reaction mixture was diluted with EtOAc (100 mL), water (100 mL) and the organic layer separated. The organic layer was dried ($MgSO_4$) concentrated to dryness in vacuo to give the title compound as an amorphous solid (2.39 g, 81%): FAB-MS 619 ($MH^+$); elemental analysis (calcd) $C_{29}H_{33}N_6O_6$: C,56.31; H, 5.38; N, 13.58. Found: C, 56.10, H, 5.51, N, 13.30.

11) Trifluoroacetyl-D-(α-methyl)phenylglycine-Azt-Arg-H.HCl

Trifluoroacetyl-D-(α-methyl)phenylglycine-Azt-Arg(Z)-H (10) (2.35 g, 3.8 mmol) was dissolved in ethanol (110 mL), water (40 mL), 1N HCl (5.7 mL), and was hydrogenated in the present of 5% Pd/C catalyst (1.1 g) at ambient, temperature and pressure of 1.5 h. After the reaction was completed, the catalyst was removed by filtration. The filtrate was concentrated to 100 mL in vacuo. An additional 50 mL of $H_2O$ and n-BuOH (100 mL) was added to the reaction mixture. The organic layer separated and the aqueous layer extracted 2 times with n-BuOH. The combined organic extracts were concentrated to dryness in vacuo. A 1:1 mixture of diethyl ether and diisopropyl ether (100 mL) was added to the reaction. The precipitate was filtered and dried in vacuo to give pure title compound (1.4 g, 71%): FAB-MS 485 (MH+); [α]$_D$= −77.6° (C=0.5/0.1N HCl).

I claim:

1. A compound of the formula

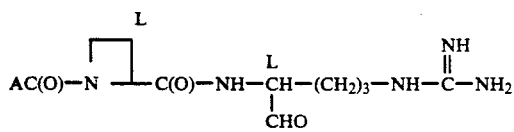

wherein A is 1) a group of the formula

wherein R is a phenyl group of the formula

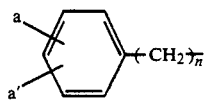

wherein a and a' independently are hydrogen, lower alkyl, lower alkoxy, halogen, trifluoromethyl, hydroxy, hydroxymethyl, amino, or aminomethyl; and n is 0 or 1; or R is thienyl, furyl, naphthyl, or naphthyl mono- or disubstituted by lower alkyl, lower alkoxy, halogen, amino, mono- or di(lower alkyl)amino, or hydroxy; or R is cyclohexadienyl, cyclohexenyl, cyclohexyl or cyclopentyl;

$R_1$ is hydrogen, methyl or ethyl;

B is lower alkyl, lower alkoxy, hydroxy, or an amino group of the formula

—N($R_2$) ($R_3$)

wherein $R_2$ and $R_3$ independently are hydrogen or lower alkyl, or $R_2$ is hydrogen, and $R_3$ is $C_1$-$C_6$ alkanoyl, halo substituted $C_2$-$C_6$ alkanoyl, or an oxycarbonyl group of the formula $R_4$—OC(O)— wherein $R_4$ is $C_1$-$C_6$ alkyl, $C_2$-$C_6$ alkenyl, $C_3$-$C_7$ cycloalkyl, benzyl, nitrobenzyl, diphenylmethyl, or a phenyl group as defined above; provided, that when $R_1$ is methyl or ethyl, B is other than methyl or ethyl and the pharmaceutically acceptable, non-toxic salts thereof.

2. The compound of claim 1 wherein A is a group of the formula

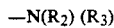

3. The compound of claim 2 wherein B is an amino group of the formula —N($R_2$) ($R_3$).

4. The compound of claim 3 wherein $R_2$ is hydrogen and $R_3$ is an oxycarbonyl group, $R_4$—O—C(O)—.

5. The compound of claim 4 wherein $R_4$ is $C_1$-$C_6$ alkyl.

6. The compound of claim 3 wherein R is a group of the formula

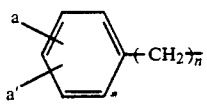

and $R_1$ is hydrogen.

7. The compound of claim 6 said compound being N-Boc-D-phenylglycyl-L-azetidinyl-L-arginine aldehyde and the pharmaceutically acceptable non-toxic salts thereof.

8. The compound of claim 6 said compound being N-Boc-D-phenylalanyl-L-azetidinyl-L-arginine aldehyde and the pharmaceutically acceptable non-toxic salts thereof.

9. The compound of claim 6 said compound being N-methyl-D-phenylalanyl-L-azetidinyl-L-arginine aldehyde and the pharmaceutically acceptable non-toxic salts thereof.

10. The compound of claim 6 said compound being N-methyl-D-phenylglycyl-L-azetidinyl-L-arginine aldehyde and the pharmaceutically acceptable non-toxic salts thereof.

11. The compound of claim 3 wherein R is naphthyl or naphthyl mono- or disubstituted and $R_1$ is hydrogen.

12. A pharmaceutical formulation which comprises an effective clot inhibiting amount of a compound of claim 1 and a pharmaceutically acceptable carrier.

13. The compound of claim 3 wherein $R_1$ is methyl or ethyl and R is a group of the formula

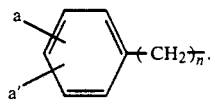

14. The compound of claim 13 wherein $R_2$ is hydrogen and $R_3$ is $C_1$-$C_6$ alkanoyl, halo substituted $C_2$-$C_6$ alkanoyl, or an oxycarbonyl group $R_4$—O—C(O)—.

15. The compound of claim 14 of the formula N-acetyl-D—Phg(α—CH$_3$)—L—Azt—L—Arg—H sulfate.

16. The compound of claim 14 of the formula N-Boc-D-Phg(α-CH$_3$)-Azt-L-Arg-H sulfate.

17. The compound of claim 14 said compound being trifluoroacetyl-D-(α-methyl)phenylglycyl-L-azetidinyl-L-arginine aldehyde and the pharmaceutically acceptable salts thereof.

18. The HCL salt of the compound of claim 17.

19. The compound of claim 14 said compound being trifluoroacetyl-D-(α-ethyl)phenylglycyl-L-azetidinyl-L-arginine aldehyde and the pharmaceutically acceptable salts thereof.

20. The HCL salt of the compound of claim 19.

21. The method for inhibiting clot formation in man and animals which comprises administering to said man or animal an effective non-toxic clot inhibiting amount of a compound of claim 1.

22. The method of claim 21 where, in the compound administered, A is

wherein R is phenyl or benzyl, $R_1$ is hydrogen and B —$N(R_2)(R_3)$ wherein $R_2$ is hydrogen and $R_3$ is lower alkyl, lower alkoxycarbonyl, or $C_1$-$C_6$ alkanoyl.

23. An intermediate of the formula

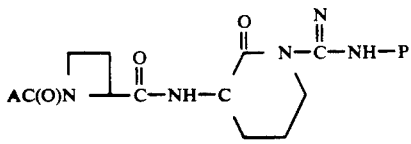

wherein A is 1) a group of the formula

wherein R is a phenyl group of the formula

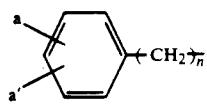

wherein a and a' independently are hydrogen, $C_1$-$C_4$ alkyl, $C_1$-$C_4$ alkoxy, halogen, trifluoromethyl, hydroxy, hydroxymethyl, amino, or aminoethyl; and n is 0 or 1;

or R is thienyl, furyl, naphthyl, or naphthyl mono- or disubstituted by lower alkyl, lower alkoxy, halogen, amino, mono- or di-($C_1$-$C_4$ alkyl)amino, or hydroxy; or R is cyclohexadienyl, cyclohexenyl, cyclohexyl or cyclopentyl;

$R_1$ is hydrogen, methyl or ethyl;

B is $C_1$-$C_4$ alkyl, $C_1$-$C_4$ alkoxy, hydroxy, or an amino group of the formula

—$N(R_2)(R_3)$ wherein $R_2$ and $R_3$ independently are hydrogen or $C_1$-$C_4$ alkyl, or $R_2$ is hydrogen, and $R_3$ is $C_1$-$C_6$ alkanoyl, halo substituted $C_2$-$C_6$ alkanoyl, or an oxycarbonyl group of the formula $R_4$—OC(O)— wherein $R_4$ is $C_1$-$C_6$ alkyl, $C_2$-$C_6$ alkenyl, $C_3$-$C_7$ cycloalkyl, benzyl, nitrobenzyl, diphenylmethyl, or a phenyl group as defined above; provided, that when $R_1$ is methyl or ethyl, B is other than methyl or ethyl and wherein P is an amino protecting group.

24. The intermediate of claim 23 wherein P is selected from the group consisting of benzyl carbonate, t-butyl carbonate, and p-toluenesulfonyl.

* * * * *